United States Patent [19]

Baxter

[11] 4,178,924

[45] Dec. 18, 1979

[54] CAST PROTECTOR

[76] Inventor: Samuel H. Baxter, 3010 Graceland Ave., Northeast, Albuquerque, N. Mex. 87110

[21] Appl. No.: 877,036

[22] Filed: Feb. 10, 1978

Related U.S. Application Data

[63] Continuation of Ser. No. 805,592, Jun. 6, 1977, abandoned, which is a continuation of Ser. No. 726,818, Sep. 27, 1976, abandoned, which is a continuation of Ser. No. 592,323, Jul. 1, 1975, abandoned.

[51] Int. Cl.² .............................................. A61F 13/00
[52] U.S. Cl. ....................................................... 128/82
[58] Field of Search .................. 128/82, 83, 83.5, 165, 128/132, DIG. 15; 2/67, 59

[56] References Cited

U.S. PATENT DOCUMENTS

| | | | |
|---|---|---|---|
| 2,244,871 | 6/1941 | Guinzburg | 128/83.5 X |
| 3,329,144 | 7/1967 | Liman | 128/82 |
| 3,480,012 | 11/1969 | Smithers et al. | 128/DIG. 15 |
| 3,504,672 | 4/1970 | Moon | 128/DIG. 15 |
| 3,741,203 | 6/1973 | Liman | 128/82 |
| 3,785,374 | 1/1974 | Lipson | 128/82 |

Primary Examiner—John D. Yasko
Attorney, Agent, or Firm—Flehr, Hohbach, Test, Albritton & Herbert

[57] ABSTRACT

An elongated tubular protective cover for a cast enclosed body limb portion is provided and at least one end of the protective cover is open and includes an elongated flexible seal band of water impervious material carried by one end of the cover and for wrapping about that end and the adjacent limb portion disposed outwardly of the cover in an edge overlapping spiral manner in order to form a fluid tight seal between the cover and the adjacent limb portion. The cover includes inner and outer telescopingly engaged tubular member constructed of flexible fluid impervious material and the inner tubular member includes features rendering it pervious to air flow therethrough. Also, at least one moisture absorptive spacing member is disposed between the outer and inner surfaces of the inner and outer tubular members. A first form of cover is closed at the end thereof remote from the flexible seal band whereby the terminal end portion of a body limb may be fully enclosed within the cover and a second form of cover is open at both ends with each end equipped with a flexible seal band.

13 Claims, 5 Drawing Figures

FIG. 3
FIG. 4
FIG. 5
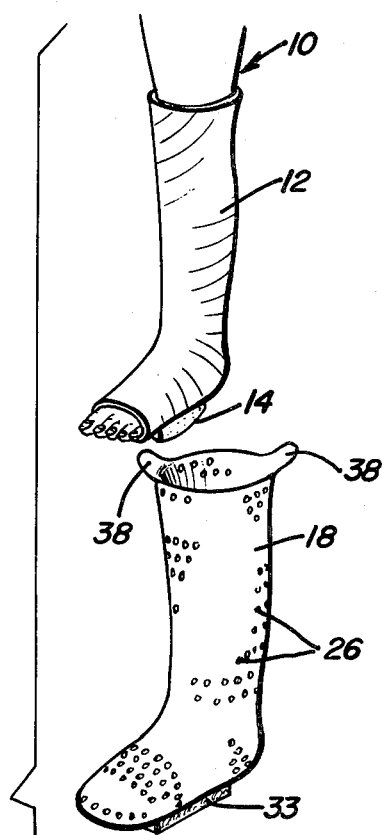
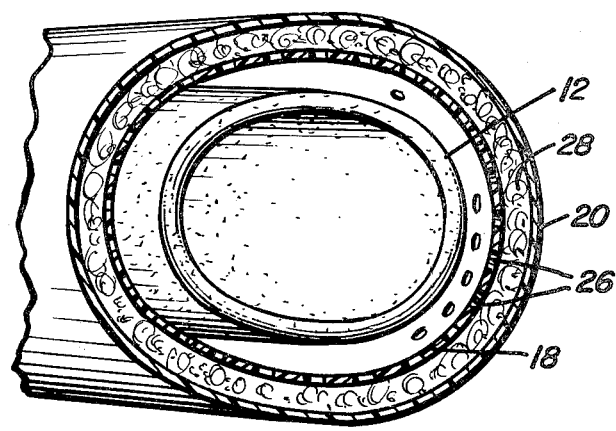
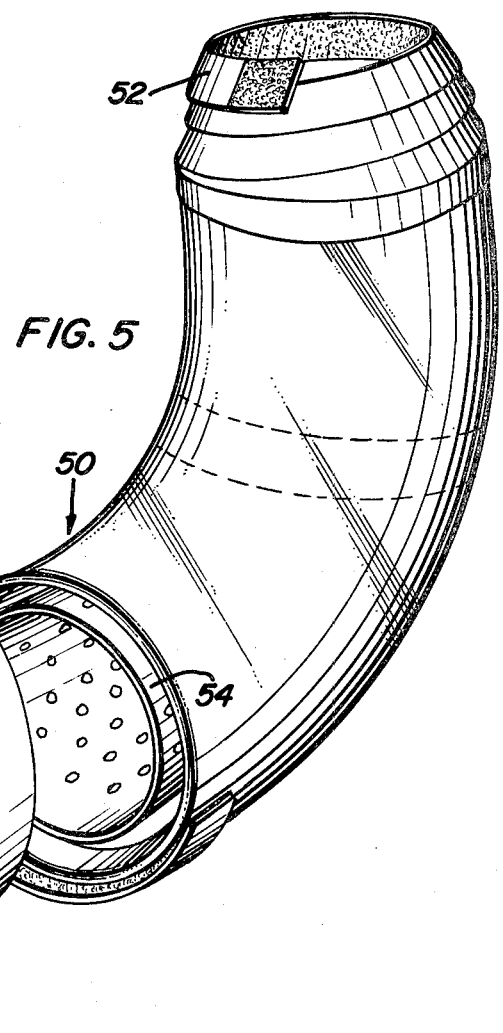

CAST PROTECTOR

This is a continuation, of application Ser. No. 805,592 filed June 6, 1977 now abandoned; which is a continuation of Ser. No. 726,818, Sept. 27, 1976; which is a continuation of 592,323, July 1, 1975, all abandoned.

BACKGROUND OF THE INVENTION

In the past various forms of protective covers for casts and adjacent limb portions have been designed and most of these previously known protective covers have, to at least some extent, offered protection against moisture in the form of rain, shower or bath water and water in a therapeutic bath. However, most previously designed covers of this type have been subject to leakage of one type or another and have not included adequate means for ventillating and/or absorbing body perspiration with the result that near 100% humidity conditions may often exist within a protective cover resulting in slow softening of the cast material as well as discomfort to the wearer of the cover.

Examples of previously patented cast protectors are disclosed in U.S. Pat. Nos. 1,908,486, 2,244,817, 3,359,658, 3,735,759, 3,741,203, 3,747,125 and 3,845,769.

BRIEF DESCRIPTION OF THE INVENTION

The protective cover of the instant invention provides a substantially water tight protective covering for a body cast and adjacent body portions projecting out of the cast. In addition an effective seal structure is provided for sealing an open end portion of the associated cast relative to the adjacent body portion. Further, means is provided within the cover for absorbing body moisture from within the cover to thereby prevent a near 100% relative humidity condition within the cover and the cover is further provided with means whereby air circulation in the area of the cover immediately about the associated cast is promoted.

The main object of this invention is to provide a cover for body casts including structure which will protect the associated cast from moisture such as may be encountered during inclement weather, while bathing and while undergoing therapeutic treatment.

Another object of this invention is to provide a protective cover in accordance with the preceding object including structure whereby air circulation within the cover immediately adjacent the exterior surfaces of the associated cast will be promoted.

Still another object of this invention, in accordance with the immediately preceding object, is to provide a protective cover including means by which moisture developed within the cover may be absorbed.

Another important object of this invention is to provide a protective cover including novel seal structure for forming a fluid tight seal between an open end portion of the cover and an adjacent body portion of the user of the cover.

A final object of this invention to be specifically enumerated herein is to provide a protective cover in accordance with the preceding objects and which will conform to conventional forms of manufacture, to be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWING

FIG. 3 is an exploded perspective view of the protective cover;

FIG. 4 is a horizontal sectional view taken substantially upon the plane indicated by the section line 4—4 of FIG. 2; and FIG. 5 is a perspective view of a second form of cover for use in conjunction with a cast open at its opposite end and with the seal structure at the lower end of the cover in an open condition.

DETAILED DESCRIPTION OF THE INVENTION

Figure 1:
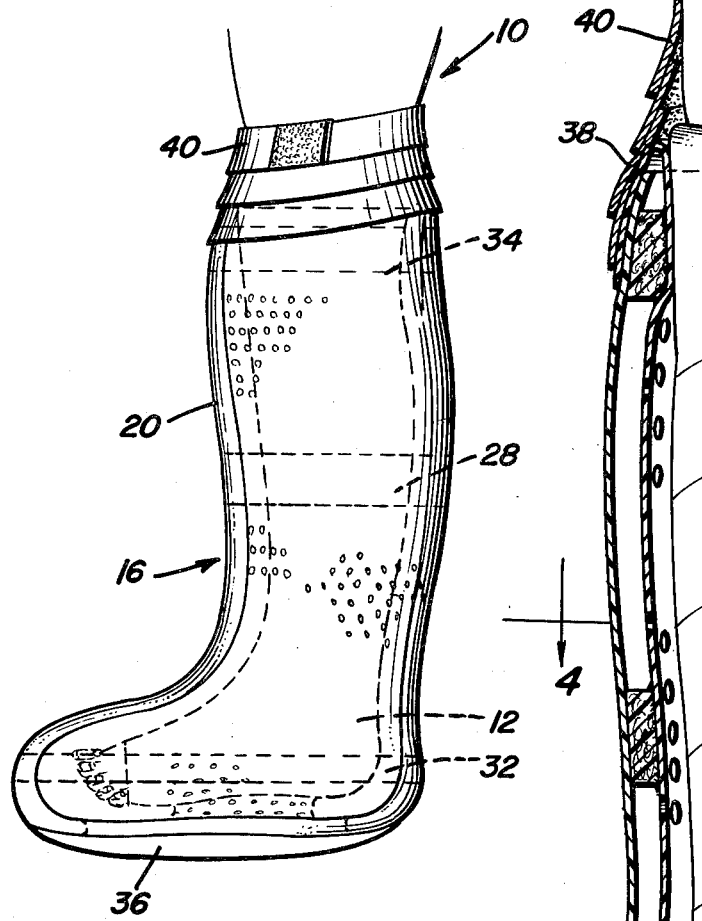
FIG. 1 is a side elevational view of a cast applied to the lower portion of the leg of a person with a first form of the cover of the instant invention applied over the cast and sealed relative to an upper leg portion of the user.

Referring now more specifically to FIGS. 1 through 4 of the drawings the numeral 10 generally designates a leg having a conventional cast 12 applied over the lower portion of the leg 10 and the attached foot portion thereof, the front area of the associated foot being open. The cast 12 is of the "walking" type in that it includes a lower pad 14 projecting below that portion of the cast 12 encircling the foot portion.

The first form of cover is referred to in general by the reference numeral 16 and includes inner and outer tubular members 18 and 20. The inner tubular member 18 includes an open upper end 22 and a closed lower end 24 and is of a size and shape to loosely enclose the cast 12. The tubular member 18 is constructed of flexible and water impervious material such as polyethelene, but is provided with a large number of small diameter breathing apertures 26. The outer tubular member 20 is of substantially the same shape, but is slightly larger than the inner tubular member 18 and loosely encloses the latter. The tubular member 20 is also constructed of flexible water impervious material such as polyethelene. Further, the tubular member 20 is devoid of openings such as the apertures 26.

A first fully encircling spacing band 28 is disposed about the tubular member 18 intermediate its opposite ends and is secured to one of the adjacent inner and outer surfaces of the outer and inner tubular members 20 and 18, respectively. Although it is not of any great importance as to which of the tubular members the band 28 is secured, the band 28 is secured to the outer surface of the tubular member 18 by any suitable adhesive 30 and the utilization of adhesive in order to secure the band 28 to the outer surface of the tubular member 18 having the apertures 26 formed therein tends to enable a more durable adhesive bond to be formed.

A second substantially continuous band 32 extends about the lower portion of the tubular member 18 between the latter and the corresponding portion of the interior of the tubular member 20. The band 32 is also secured by adhesive 30 to the outer surface of the tubular member 18. Furthermore, a pad 33 is disposed between the closed ends of the tubular members 18 and 20 and may be adhesively bonded to both the inner surface of the tubular member 20 and the outer surface of the tubular member 18. Finally, a third band 34 is disposed between the tubular members 18 and 20 adjacent the open ends thereof and is bonded to the outer surface of the tubular member 18 by means of adhesive 30.

The bands 28,32 and 34 are constructed of resilient material having moisture absorbing properties, or may be constructed of foam rubber impregnated with a moisture absorbing material such as silica gel. Also, the pad 33 may be constructed of substantially the same material.

The lower outer surface of the tubular member 20 has a wear resistant resilient pad 36 bonded thereto and the cover 16 may thus be used in conjunction with the walking cast 12.

From FIG. 3 of the drawings it may be seen that opposite side portions of the upper end of the inner tubular member 18 include upwardly extending ear portions 38 and these ear portions 38 are downturned over the corresponding upper end portion of the outer tubular member 20 and thermo welded thereto. The remaining portions of the upper ends of the tubular members 18 and 20 between the ear portions 38 are open whereby air circulation from the exterior of the cover 16 and between the inner and outer surfaces of the outer and inner tubular members 20 and 18 may be caused by any suitable means when the cover 16 is not in use.

Figure 2:
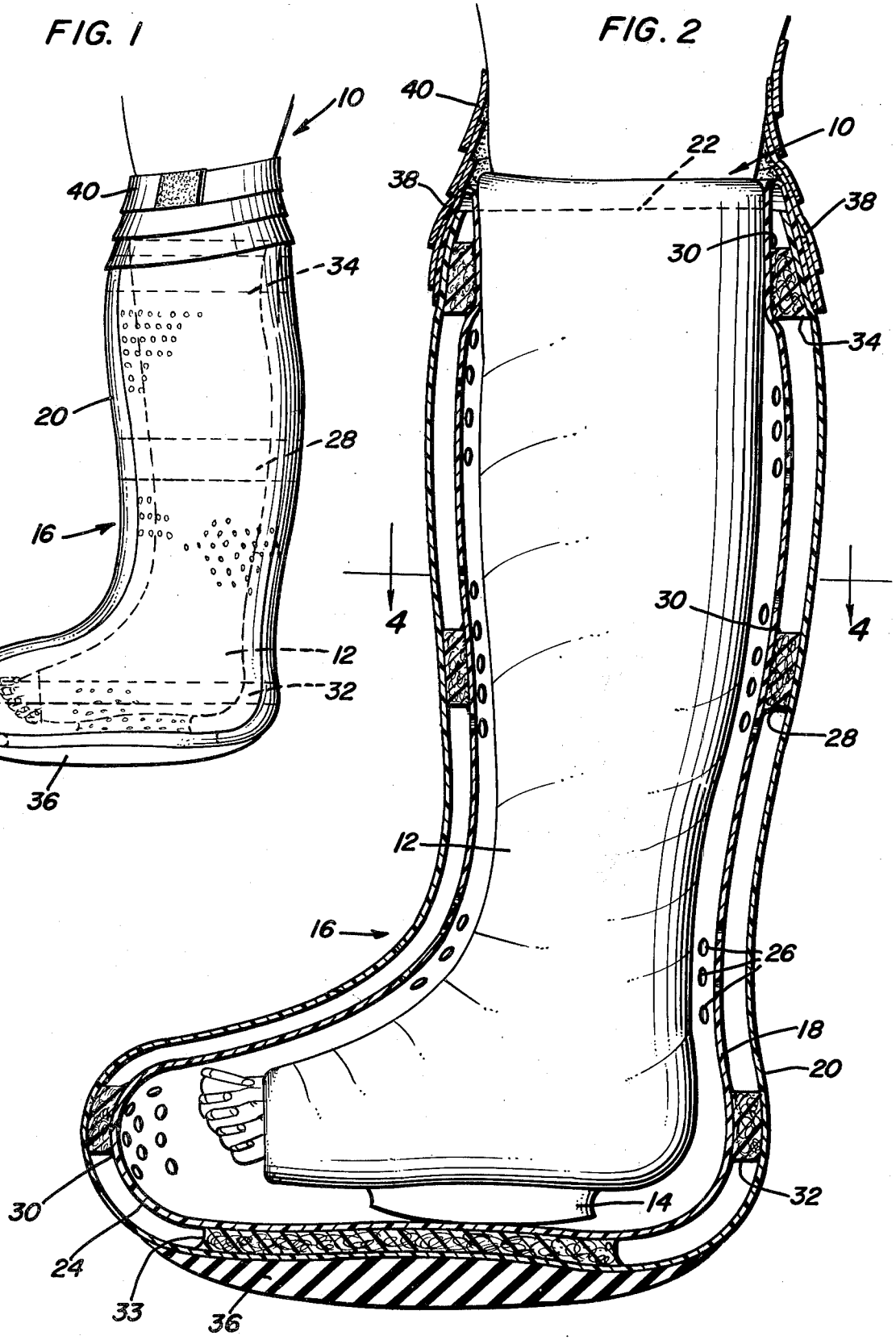
FIG. 2 is an enlarged vertical sectional view of the assemblage illustrated in FIG. 2.

In use the cover 16 is applied over the lower leg portion and the cast 12 in the manner illustrated in FIG. 2 of the drawings. An elongated flexible strip 40 of water impervious material such as polyethelene has one end thereof secured to an upper portion of the outer tubular member as at 42 and the strip 40 is thereafter wound about the upper portion of the tubular member 20 in a spiral edge overlapping manner and up onto the adjacent portion of the leg 10 in a manner to define a fluid tight overlapping seal between the leg 10 and the outer tubular member 20. Thus, moisture from the exterior of the cover 16 may not enter the latter and the user of the cover 16 is assured that rain, bath and shower water will not penetrate the cover 16.

Further, inasmuch as the bands 28, 32 and 34 retain the outer tubular member 20 spaced outwardly of the tubular member 18 and movement of the associated limb will cause at least some flexure of the outer tubular member 20 relative to the inner tubular member 18, air circulation between the interior of the inner tubular member 18 and the exterior of the inner tubular member interiorly of the outer tubular member 20 will be effected. Thus, any body moisture developing within the inner tubular member 18 is at least to some degree purged therefrom and absorbed by the absorbent bands 28, 32 and 34. When the cover 16 is not in use it may be positioned so as to cause a circulation of air through the interior of the inner tubular member 18 and outward through the open upper ends of the tubular member 10 and 20 to thereby dry the moisture absorbtive bands 28, 32 and 34 prior to the next use of the cover 16.

Inasmuch as the upper portion of the cover 16 is sealed relative to the upper leg portion by means of the strip 40, if the inside diameter of the open end of the cover 16 is appreciably larger than the outside diameter of the upper end of the cast 10, the cover 16 is merely folded over prior to final positioning of the seal strip 40 in order to form a dart in the upper portion of the cover 16 whereby the upper end of the cover will tightly embrace the outer surface of the upper end of the cast 12.

Referring now more specifically to FIG. 5 of the drawings, a modified form of cover is referred to in general by the reference numeral 50. The cover 50 is substantially identical to the cover 16 except that both ends of the cover 50 are open and equipped with a seal strip 52 corresponding to the seal strip 40. Further, both ends of the inner tubular member 54 of the cover 50 may be equipped with tabs corresponding to the tabs or ear portions 38 and it will be noted from a comparison of FIGS. 3 and 5 that the overall shape of the cover 50 is different from the overall shape of the cover 16. Of course, the cover 50 is adapted to be used in conjunction with a cast formed about the elbow area and adjacent upper and lower arm portions. Still further, both ends of the cover 16 could be open if the lower end of the cast 12 was sufficiently foreshortened to enable a second seal strip such as the strip 40 to be utilized in forming a seal between the lower open end of the cast 12 and the associated foot portion.

It is now seen that the protective devices herein described and illustrated achieve more than adequate protection for practical use and meet the required objectives of the invention. The invention may also be used on animals under similar conditions herein stated. As other combinations of the construction of the invention herein described are possible, it is to be understood that all matter shown in the enclosed drawings are merely illustrative, and do not limit the inventor to the invention herein described except as may be required by the appended claims.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In combination, an elongate tubular protective cover for a cast enclosed body limb portion to be inserted into said cover from one open end thereof and with said one end including seal means for forming a substantially fluid tight seal between said one end of said cover and the adjacent body limb portion, said cover comprising inner and outer telescopingly engaged tubular members constructed of flexible material, said inner tubular member including means rendering it pervious to air flow therethrough, said outer tubular member being impervious to the flow of liquids therethrough, at least one substantially continuous band member disposed between said inner and outer tubular members, intermediate their opposite ends, and secured to one of the opposing outer and inner surfaces thereof, said band member including means for absorbing moisture and comprising means to maintain at least the adjacent portions of said inner and outer tubular members spaced apart.

2. The combination of claim 1, wherein said seal means including the other end of said cover is also open.

3. The combination of claim 1, wherein an elongated flexible seal band of water impervious material carried by said one end for wrapping about said one end of said cover and the adjacent limb portion disposed outwardly of said one end of said cover in an edge overlapping spiral manner in order to form a fluid tight seal between said cover and the adjacent limb portion.

4. The combination of claim 3, wherein the other end of said cover is also open, said other open end of said cover also having an elongated flexible seal band carried thereby and operatively associated therewith.

5. The combination of claim 1, wherein the ends of said tubular members defining the other end of said cover are closed and define a closed end thereof.

6. The combination of claim 1 and including a resilient body disposed between and supported from one of the opposing outer and inner surfaces of the closed ends of said tubular members.

7. The combination of claim 6, wherein said resilient body includes means for absorbing moisture.

8. The combination of claim 1, wherein said inner tubular member is constructed of water impervious material and said means rendering said inner tubular member pervious to air flow thereto comprises a plurality of small openings formed through the water impervious material of said inner member.

9. The combination of claim 1, wherein corresponding diametrically opposed portions of the ends of said tubular members are secured together at said one end of said cover.

10. In combination, an elongated tubular protective cover for a cast enclosed body limb portion to be inserted into said cover from one open end thereof and with said one end including seal means for forming a substantially fluid tight seal between said one end of said cover and the adjacent body limb portion, said cover comprising inner and outer telescopingly engaged tubular members constructed of flexible material, said inner tubular member including means rendering it pervious to air flow therethrough, said outer tubular member being impervious to the flow of liquid therethrough, and spacing members supported between corresponding portions of said tubular members from at least one of said members, said spacing members including means for absorbing moisture and functioning to maintain at least the adjacent portions of said inner and outer tubular members spaced apart.

11. The combination of claim 10 wherein the ends of said tubular members defining said other end of said cover are closed and define a closed end of said cover, said spacing members including a spacing member disposed between the opposing surfaces of said closed ends of said tubular members.

12. The combination of claim 10 wherein peripherally spaced sets of corresponding portions of the ends of said tubular members defining the open end of said cover are secured together and the remaining corresponding portions of said tubular members at said open end of said cover are free of direct securement to each other, whereby air circulation between the inner and outer tubular members may be readily effected when the protective cover is not in use.

13. In combination, an elongated tubular protective cover for a cast enclosed body limb portion to be inserted into said cover from one open end thereof and with said one end including seal means for forming a substantially fluid tight seal between said one end of said cover and the adjacent body limb portion, said cover comprising inner and outer telescopingly engaged tubular members constructed of flexible material, said inner tubular member including means rendering it pervious to air flow therethrough, said outer tubular member being impervious to the flow of liquid therethrough, and spacing members supported between corresponding portions of said tubular members from at least one of said members, and comprising means to maintain at least the adjacent portions of said inner and outer tubular members spaced apart.

* * * * *